(12) United States Patent
Leake et al.

(10) Patent No.: US 11,931,283 B2
(45) Date of Patent: Mar. 19, 2024

(54) METHOD AND APPARATUS FOR SPINAL DISC DECOMPRESSION

(71) Applicant: VERTECORE TECHNOLOGIES LLC, Crosby, MS (US)

(72) Inventors: Paul H. Leake, Crosby, MS (US); Paul R. Montalvo, Lewisville, TX (US)

(73) Assignee: Vertecore Technologies, LLC, Crosby, MS (US)

( * ) Notice: Subject to any disclaimer, the term of this patent is extended or adjusted under 35 U.S.C. 154(b) by 76 days.

(21) Appl. No.: 15/092,545

(22) Filed: Apr. 6, 2016

(65) Prior Publication Data

US 2016/0296361 A1 Oct. 13, 2016

Related U.S. Application Data

(60) Provisional application No. 62/144,958, filed on Apr. 9, 2015.

(51) Int. Cl.
*A61F 5/048* (2006.01)
*A61H 1/02* (2006.01)

(52) U.S. Cl.
CPC .......... *A61F 5/048* (2013.01); *A61H 1/0218* (2013.01); *A61H 1/0292* (2013.01); *A61H 2201/1207* (2013.01); *A61H 2201/1238* (2013.01); *A61H 2201/1253* (2013.01); *A61H 2201/1436* (2013.01); *A61H 2201/1623* (2013.01); *A61H 2201/1628* (2013.01); *A61H 2201/1645* (2013.01); *A61H 2201/165* (2013.01);
(Continued)

(58) Field of Classification Search
CPC .. A61F 5/048; A61F 5/01; A61F 5/024; A61F 5/026; A61F 5/028; A61F 5/03; A61H 1/0292; A61H 2201/1207; A61H 2201/1238; A61H 2201/1253; A61H 2201/1436; A61H 2201/1623; A61H 2201/1628
USPC ................................. 602/5, 19, 36
See application file for complete search history.

(56) References Cited

U.S. PATENT DOCUMENTS

| | | | |
|---|---|---|---|
| 2,642,306 A * | 6/1953 | Beeler | E01H 1/12 294/61 |
| 2,835,247 A | 5/1958 | Stabholc | |

(Continued)

FOREIGN PATENT DOCUMENTS

| | | |
|---|---|---|
| CN | 2038378 U | 5/1989 |
| CN | 2053093 U | 2/1990 |

(Continued)

OTHER PUBLICATIONS

Vertetrac—Vertetrac Ambulatory 3D Traction. Retrieved from https://web.archive.org/web/20150328164355/http://meditrac.co.il/products/vertetrac.

*Primary Examiner* — Caitlin A Carreiro
(74) *Attorney, Agent, or Firm* — Butler Snow LLP; Jon E. Holland (57) ABSTRACT

A portable spinal decompression device includes a top (thoracic) adjustable belt and bottom (lumbar) adjustable belt with a plurality of traction devices attached at set anchor points for applying traction forces to a body to facilitate spinal disc decompression and alleviate pain of users with spinal disorders. The portable device that fits various shapes and body sizes can be operated by a user without additional assistance and can be used while the individual is in numerous positions during his or her daily routine.

16 Claims, 9 Drawing Sheets

(52) U.S. Cl.
CPC ............... *A61H 2201/1664* (2013.01); *A61H 2201/1697* (2013.01)

(56) References Cited

U.S. PATENT DOCUMENTS

| | | | |
|---|---|---|---|
| 3,889,664 | A | 6/1975 | Heuser et al. |
| 3,926,182 | A * | 12/1975 | Stabholz ................. A61F 5/024 |
| | | | 602/36 |
| 4,715,362 | A * | 12/1987 | Scott ....................... A61F 5/024 |
| | | | 602/19 |
| 4,721,102 | A * | 1/1988 | Pethybridge ............ A61F 5/024 |
| | | | 602/19 |
| 4,987,885 | A * | 1/1991 | Shtabholz ............... A61F 5/024 |
| | | | 606/241 |
| 5,651,764 | A | 7/1997 | Chiu |
| 5,916,188 | A | 6/1999 | Ousdal |
| 6,280,405 | B1 | 8/2001 | Broselid |
| 6,533,740 | B2 | 3/2003 | Reinecke et al. |
| 7,144,380 | B2 | 12/2006 | Gilliam |
| 7,276,038 | B2 * | 10/2007 | Reinecke ................. A61F 5/028 |
| | | | 602/19 |
| 7,445,608 | B2 | 11/2008 | Dunfee et al. |
| 2002/0123705 | A1 | 9/2002 | Reinecke et al. |
| 2004/0073150 | A1 * | 4/2004 | Roballey ................. A61F 5/024 |
| | | | 602/36 |
| 2006/0161085 | A1 | 7/2006 | Wikenheiser et al. |
| 2009/0036888 | A1 | 2/2009 | Dunfee et al. |
| 2014/0214044 | A1 | 7/2014 | Robinson |

FOREIGN PATENT DOCUMENTS

| | | |
|---|---|---|
| CN | 2351111 Y | 12/1999 |
| CN | 2676868 Y | 2/2005 |
| CN | 200939192 Y | 8/2007 |
| CN | 201026255 Y | 2/2008 |
| CN | 201524158 U | 7/2010 |
| KR | 2005-0013085 A | 2/2005 |
| KR | 10-1138911 B1 | 7/2012 |
| KR | 2014-0013861 A | 2/2014 |

* cited by examiner

METHOD AND APPARATUS FOR SPINAL DISC DECOMPRESSION

CROSS-REFERENCES TO RELATED APPLICATIONS

This application claims the benefit of U.S. Provisional Application No. 62/144,958, filed Apr. 9, 2015, which is incorporated herein by reference in its entirety.

FIELD OF THE INVENTION

The present invention is generally directed toward therapeutic decompressions. More specifically, it relates to an apparatus and method that promotes spinal disc decompression.

BACKGROUND OF THE INVENTION

The basic principles of spinal traction have been offered by chiropractors, osteopaths, and other appropriately trained health professionals for many years. Both traction and decompression therapy are applied with the goal of relieving pain and promoting an optimal healing environment for bulging, degeneration or herniated discs. Pain relief is a result of creating a negative intradiscal pressure to promote retraction or repositioning of the herniated or bulging disc material and/or creating a lower pressure in the disc that will cause an influx of healing nutrients and other substances into the disc. Additionally, spinal decompression is used to relieve pressure on the spinal cord or one or more compressed nerve roots passing through the spinal column. Decompression of the spinal neural elements is a key component in treating spinal disorders such as radiculopathy, myelopathy and claudication.

Spinal decompression therapy involves stretching the spine, using traction or a motorized device, with the goal of relieving back pain. Devices that apply traction forces to the body to facilitate spinal disc decompression and provide relief to individuals in back pain are known in the art. However, the current decompression devices are bulky, difficult to operate, and require the user to stay in a single position in a single location, such as lying face down on a table. Also, the current devices are limited to a specific body type and thus, not available to individuals who may be suffering the most. Therefore, the need exists for a decompression device that is portable and allows the user to carry on normal daily activities while providing therapeutic relief to the user.

SUMMARY OF THE INVENTION

The invention generally relates to a portable decompression device that provides traction and decompression therapy that relieves pain and promoting an optimal healing environment for bulging, degeneration or herniated discs. The device is comprised of a top (thoracic) adjustable belt and bottom (lumbar) adjustable belt with a plurality of traction devices attached at set anchor points for applying traction forces to a body to facilitate spinal disc decompression.

BRIEF DESCRIPTION OF THE DRAWINGS

Further advantages of the invention will become apparent by reference to the detailed description of preferred embodiments when considered in conjunction with the drawings.

DETAILED DESCRIPTION

The following detailed description is presented to enable any person skilled in the art to make and use the invention. For purposes of explanation, specific details are set forth to provide a thorough understanding of the present invention. However, it will be apparent to one skilled in the art that these specific details are not required to practice the invention. Descriptions of specific applications are provided only as representative examples. Various modifications to the preferred embodiments be readily apparent to one skilled in the art, and the general principles defined herein may be applied to other embodiments and applications without departing from the scope of the invention. The present invention is not intended to be limited to the embodiments shown, but is to be accorded the widest possible scope consistent with the principles and features disclosed herein.

This device solves the problems existing in the art by providing users a portable solution which they can operate while completing their normal daily activities. Unlike prior decompression devices which require users to remain in a single position without moving while receiving treatment from a second individual, this portable device can be operated and worn by users while driving, walking, working on a computer, sitting, cooking, etc. Furthermore, this invention provides pain relief to individuals with many different body shapes and sizes. For example, the device can be worn by children, athletes, and/or obese individuals who may be suffering the most from spinal disc pain.

Figure 1:
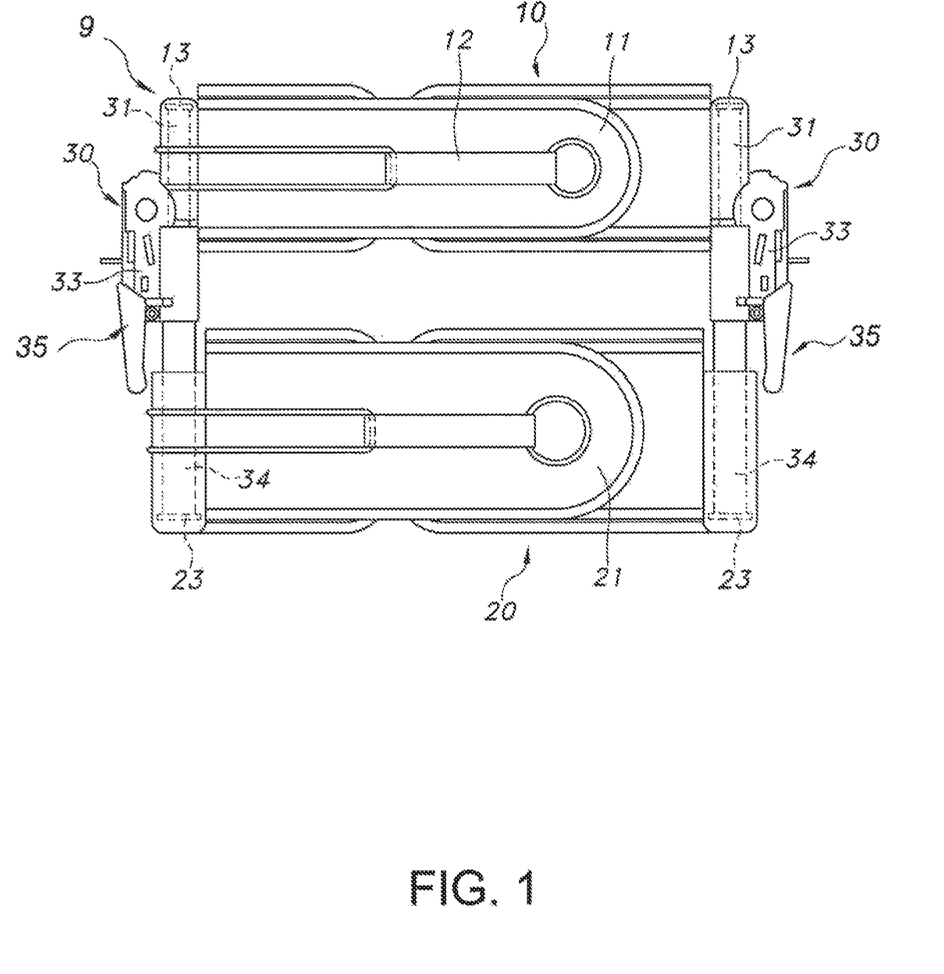
FIG. 1 is a front view of the device collapsed in neutral or start position.

Referring to the drawings, as shown in FIG. 1, the device 9 consists of adjustable belts 10, 20 and a traction tensioner assembly 30 with a plurality of traction devices at set anchor points to allow for elongation and decompression of toothed rods 32 while on a user.

In the preferred embodiment of the device, the thoracic belt 10 is designed to encircle the torso and serves as the host for the top vertical anchor points 13 for extension or decompression. The lower lumbar belt 20 is designed to encircle the waist area and serves as the host for the lower vertical anchor points 23 for extension or decompression. Top vertical anchor points 13 and lower vertical anchor point 23 are attached or positioned into the top thoracic belt 10 and lower lumbar belt 20 respectively.

Both belts, the thoracic belt 10 and lumbar belt 20 are adjustable such that they can accommodate people of larger girths. In a preferred embodiment, the belts are adjoined by hook and loops which allow the position of the decompression rods 32 to be adjusted forward or back along the belts to accommodate a wide range of user sizes and body types and enhance the device's use as a treatment tool certain spinal disorders such as scoliosis.

The belts 10, 20 can be made of any material that has stretchable as well as fixed fibers which allow them to form, contour or wrap around the thoracic or chest region and waist regions. Preferably, the material is a breathable material such as nylon.

Also, the belts can be securely fastened and adjoined by mechanisms other than the hook and loop, such as clasps, buckles, snaps or any other type of adjoinment.

The belts may also include molded pieces, padding or inserts for greater comfort, tighter fits or more precise movement and adjustments. However, the belt design is not required for the present invention, and any other mechanisms capable of securing the traction tensioner assembly to the user are contemplated by this invention.

The decompression device operates by extending the distance between the two belts. Mechanisms for extending a rod 32 or exerting pressure between top and bottom anchor points 13, 23 such as hydraulic, pneumatic, electric or mechanical may be used in other embodiments of the present invention.

However, in the preferred embodiment, the traction tensioner assembly 30 serves as the connecting element between anchor points 13, 23 incorporated in the thoracic belt 10 and the lumbar belt 20 as well as the element to apply force utilized for extension or decompression. The traction tensioner assembly 30 allows the user to exert reasonable lift or force needed to decompress and then return to a neutral position by way of a user operated ratchet type actuator mechanism and incorporated release. When in use, the ratchet type actuator moves bi-directionally along the toothed rods 32 when lift or force is exerted upon the actuator handles 35 by the user.

To assemble the preferred embodiment of the device, the thoracic belt 10, containing at least two top anchor points 13 is inserted with the upper end 31 of two traction tensioner assemblies, one assembly for each anchor point inserted to form 90 degree angles. The lumbar belt 20, likewise containing at least two lower anchor points 23, is inserted with the lower portion of the same two traction tensioner assemblies 34, thus holding the two traction tensioner assemblies 30 on each side of the adjustable belts 10, 20 and parallel to each other.

The user first attaches the upper thoracic belt 10 around their chest, positioning close up in the axilla (armpit) area and adjusts said belt 10 for a tight fit using an elastic hook and loop closure of the thoracic inner wrap belt 11. The outer tension adjustment 12 can further be cinched to ensure a snug custom fit. The two top anchor points 13 attached to the belt on opposite halves are positioned snuggly within the recess of the axilla.

Figure 2:
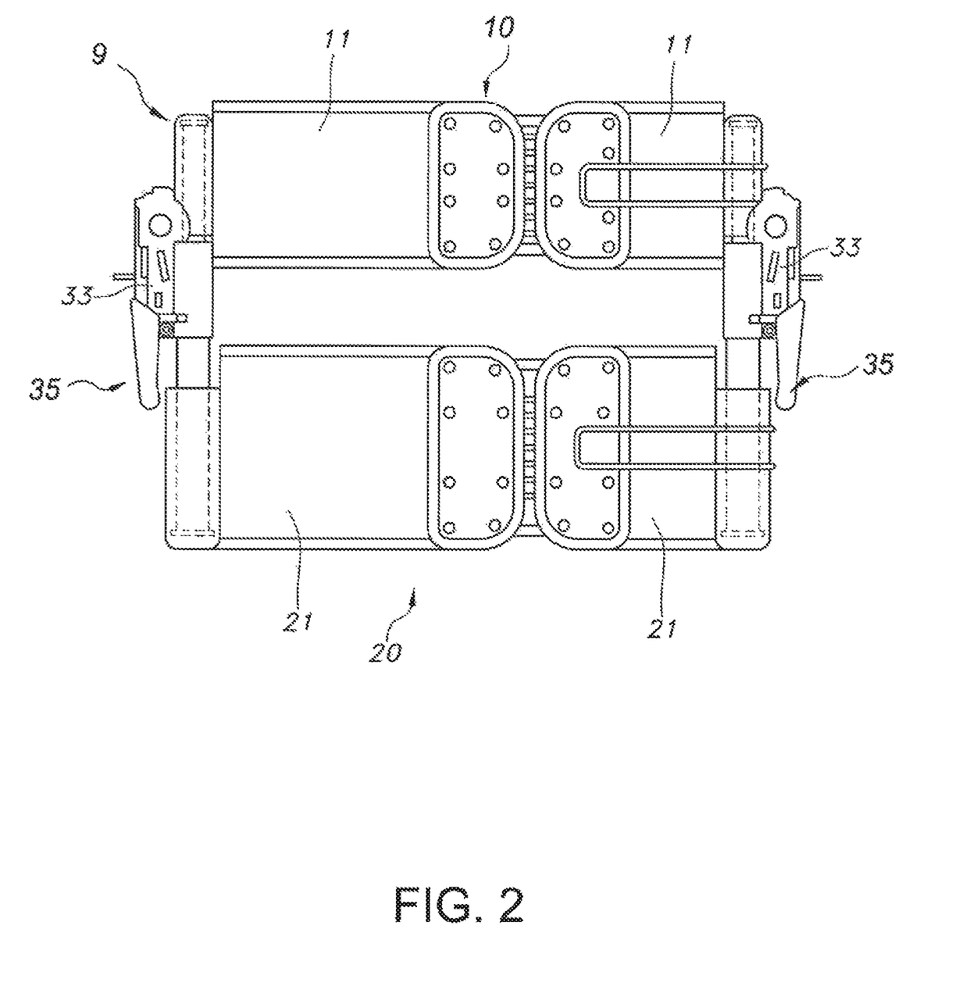
FIG. 2 is a rear view of the device collapsed in neutral or start position.

Next, the bottom lumbar belt 20 is placed around the waist and adjusted for a tight fit using the elastic hook and loop closure of the lumbar inner wrap belt 21. The user will note that the traction tensioner assembly 30 on each side runs from the axilla toward the hip and parallel to the body. As shown in FIGS. 1 and 2, once the user has finished attaching the device 9, it is compressed in neutral or start position.

Figure 7:
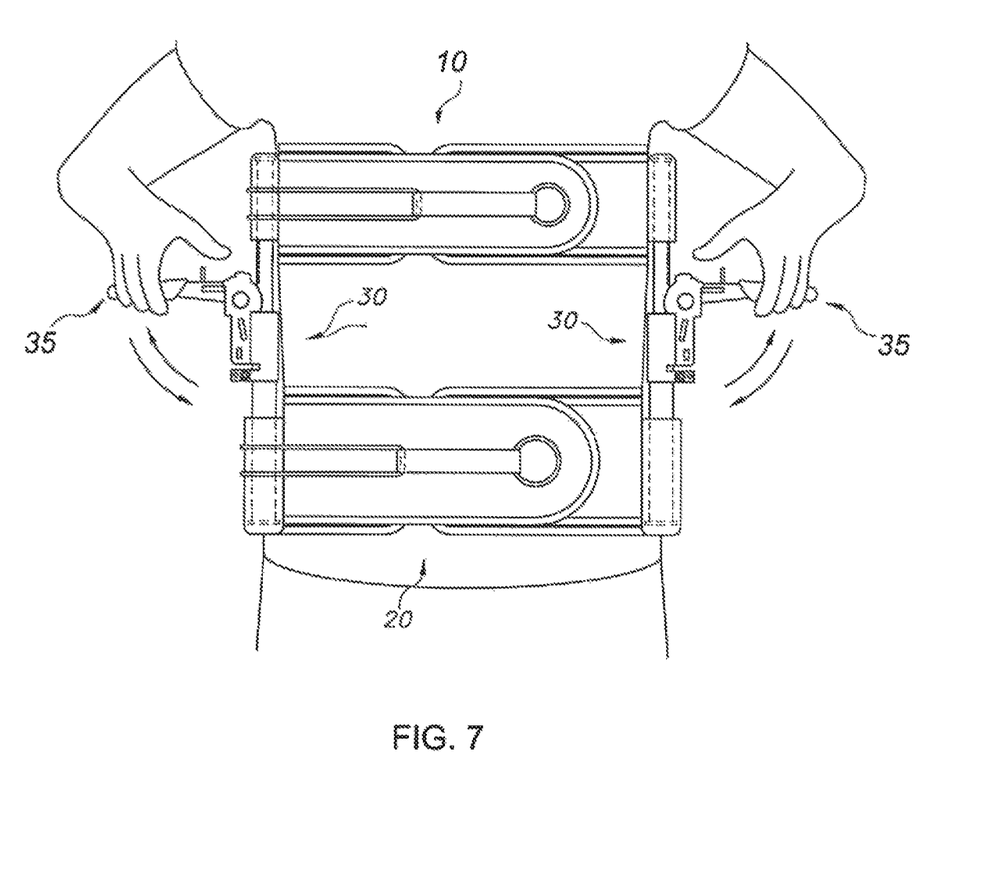
FIG. 7 is a front view of the device in the process of decompressing by a user.

To extend the traction tensioner assembly 30 and begin decompression as shown in FIG. 7, the user simply grasps the incorporated actuator 33 with quick release handle 35 on the side of each traction tensioner assembly 30, raising and lowering the handles 35 in a back and forth ratchet action. An audible ratcheting sound confirms the extending action of the along the toothed rods 32 caused by stroking the handles 35.

Figure 3:
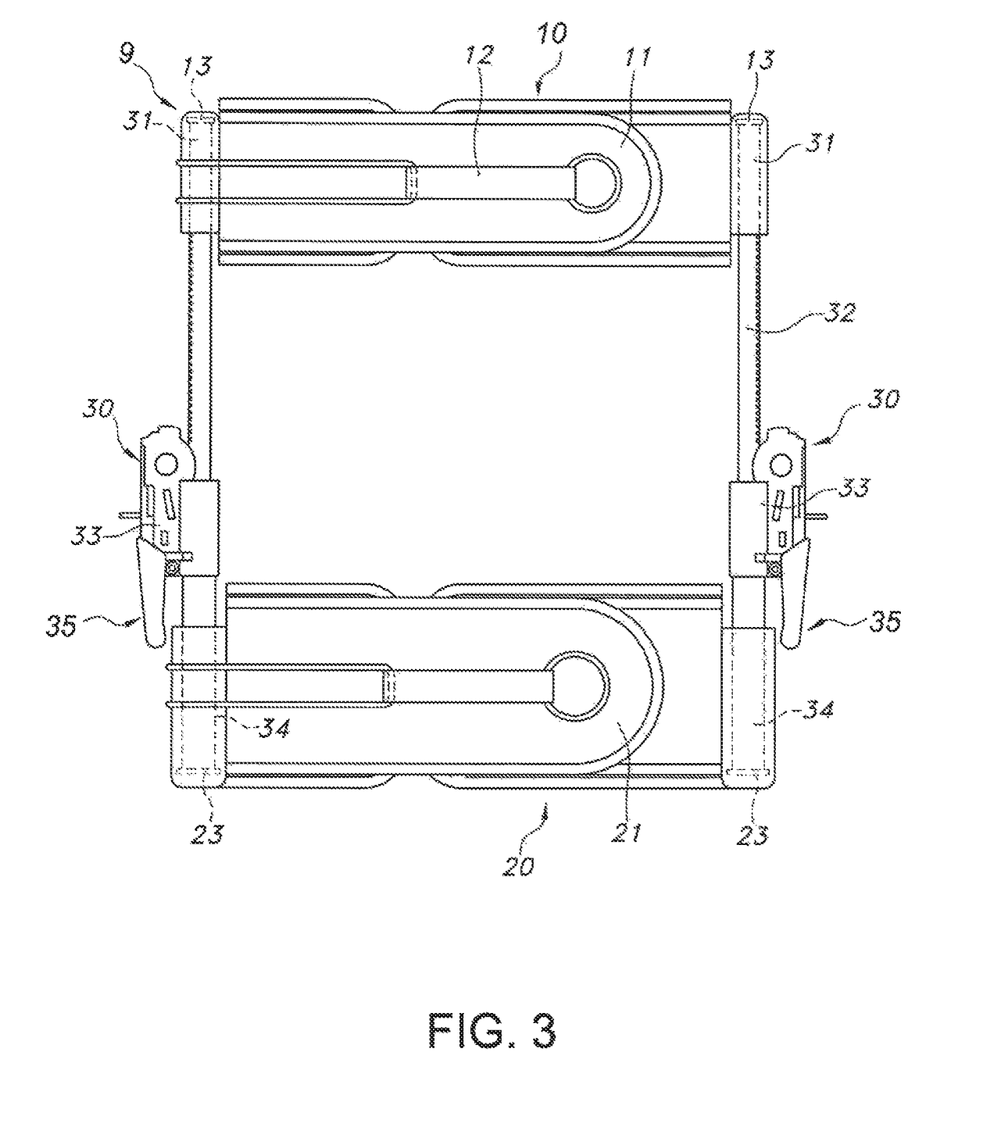
FIG. 3 is a front view of the device extended for decompression with traction tensioner assembly handles in normal down position.
Figure 4:
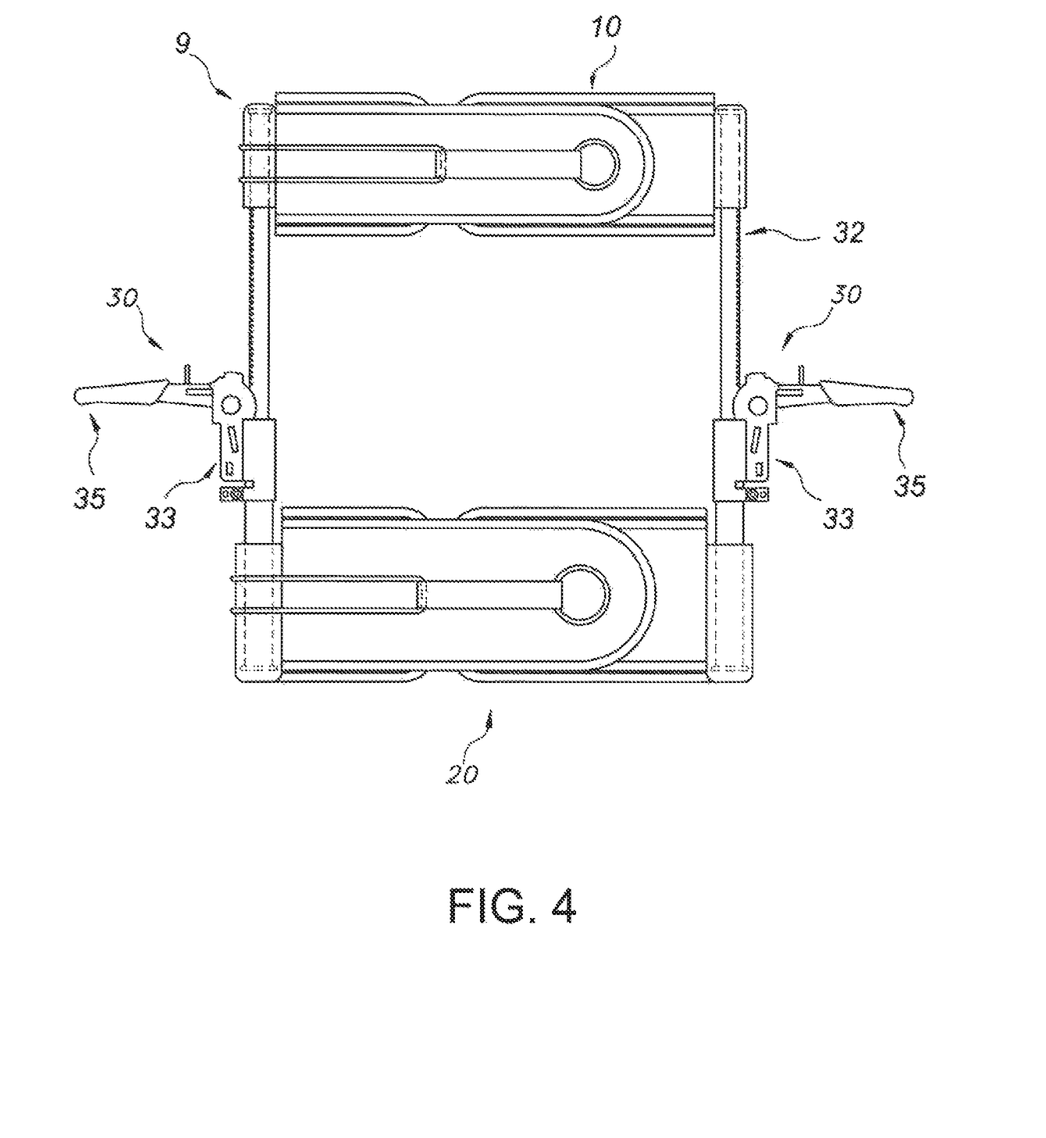
FIG. 4 is a rear view of the device extended for decompression.
Figure 5:
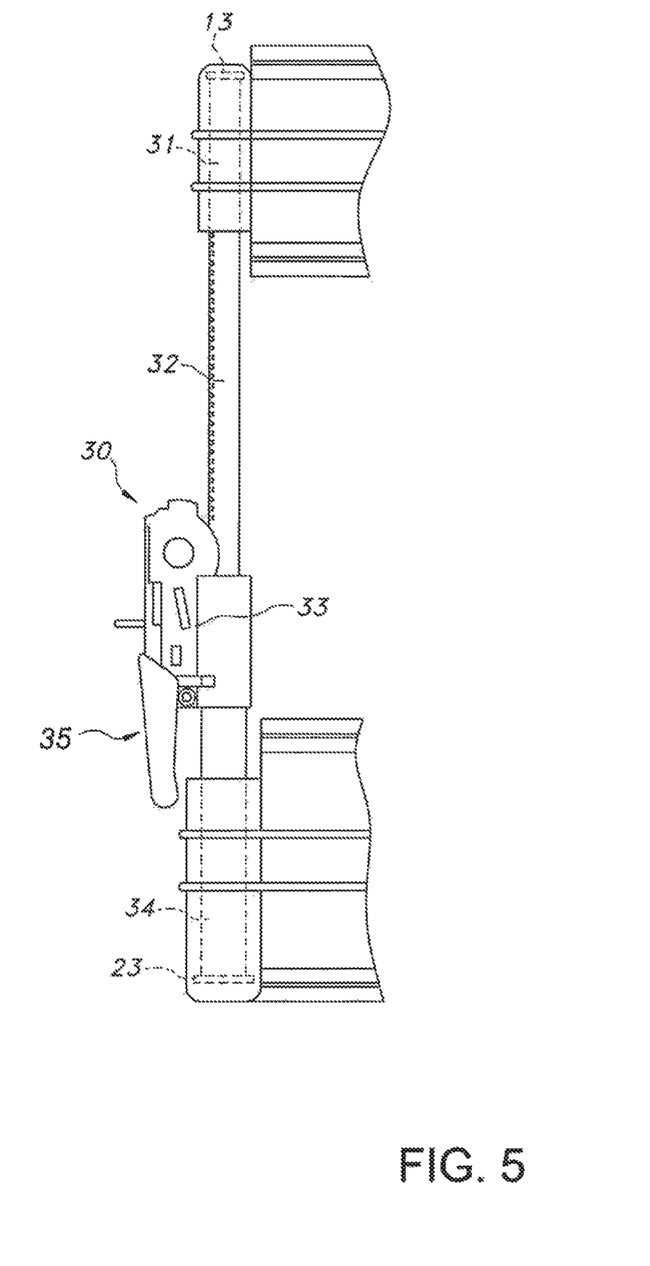
FIG. 5 is a right side view of the device with the traction tensioner assembly as extended and with handle in downward neutral position.
Figure 6:
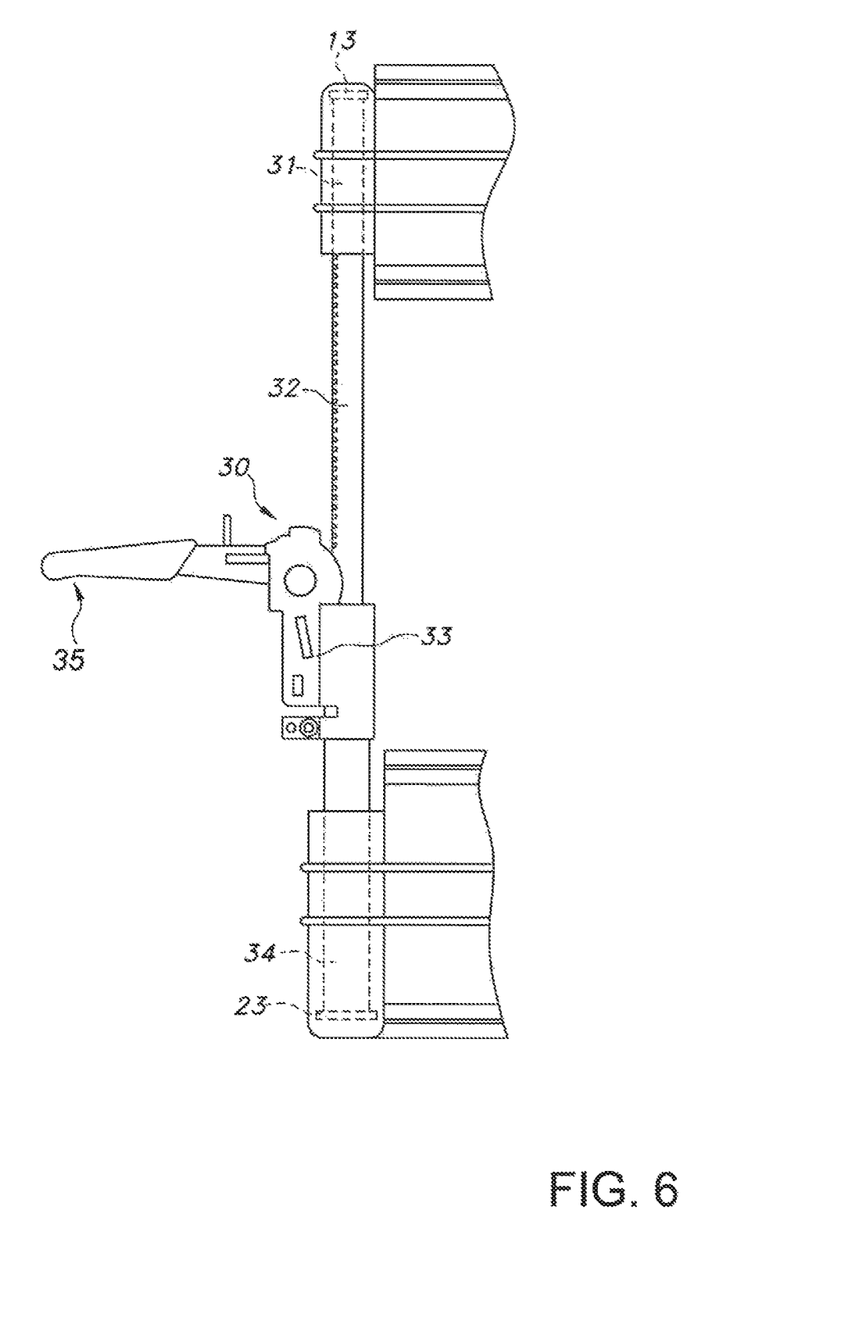
FIG. 6 is a right side view of the device with traction tensioner assembly extended and handle in upright positive position.
Figure 8:
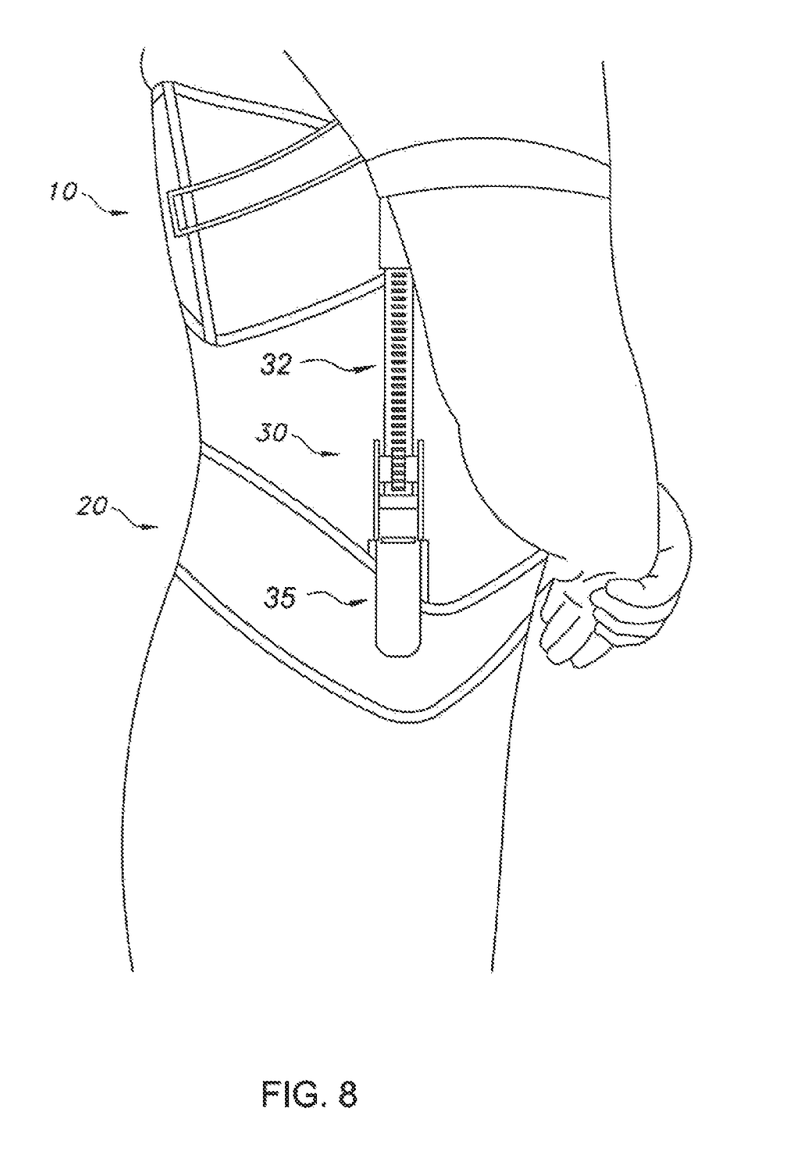
FIG. 8 is a side view of the device decompressed with traction tensioner assembly extended to provide decompression while the user is standing upright.
Figure 10:
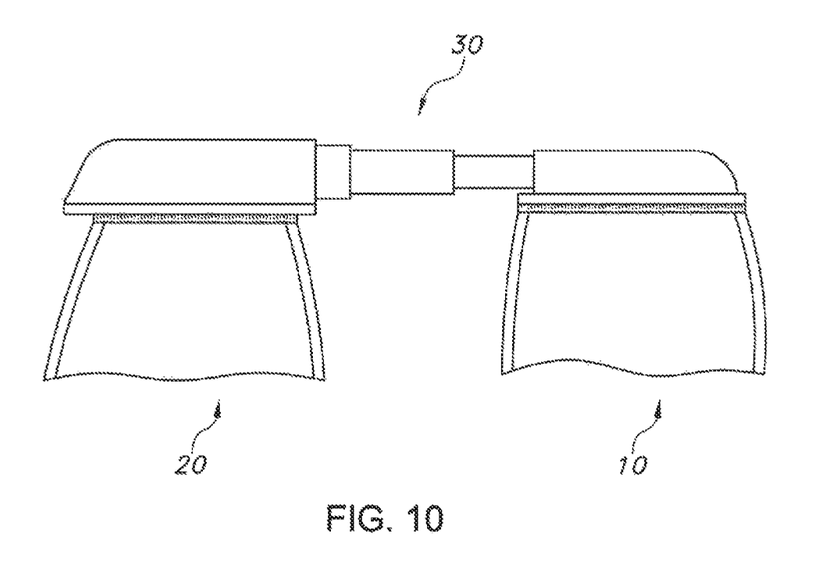
FIG. 10 is a side view of an embodiment of the device.

As the respective belts 10, 20 tighten against their anchor points 13, 23, decompression will begin as the spinal column is relieved of pressure. As shown in FIG. 4, when the handles are upright or in a positive position, the device is ready for the user to stroke the handles 35 down to apply more tension. Alternatively, as shown in FIGS. 3 and 10, the handles 35 are placed in a down position when the user feels they have reached a point of relief or decompression. After reaching this point of relief, as shown in FIG. 8, the users can continue their normal daily activities in in most any position such as standing, sitting, or laying.

Once the user feels relief or that they have sufficiently decompressed for one session, it is simply a matter of activating the quick release 35 on each traction tensioner assembly 30 actuator 33 to return the unit to a neutral position. The adjustable belts 10, 20 are removed in easy fashion, opposite from how they were put on and the entire unit is easily stored until the next use.

The anchor points 13, 23 which receive and transfer force for decompression can be fixed and utilized in various embodiments and of varying materials, including as illustrated in adjustable belts or in vests, single and dual point anchors which are transportable between utility style belts and various harnesses.

Figure 9:
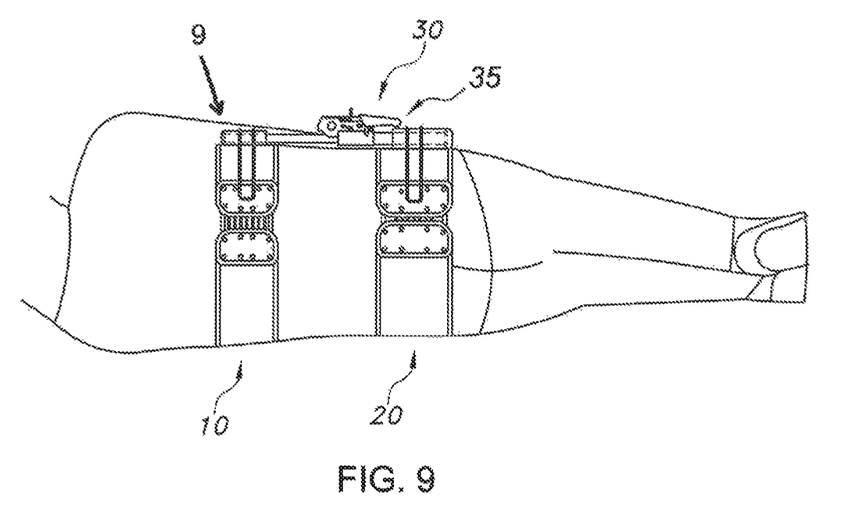
FIG. 9 is a rear view of the device with the user decompressed and resting on his or her side.

As shown in FIG. 9, a potential embodiment of the device 9 includes using rods 32 with telescoping stock to further reduce the height requirements of the rod 32 lengths when in a neutral starting position and further increase the range of individual users able to use the device 9.

A potential embodiment of the device provides an audible indicator when extension or decompression is being initiated, engaged or proceeding, with or without electronic readout for certain indicators such as pounds of force, time duration or length of extension.

The device can also be used to alleviate pain in different areas of the body. For instance, the device can be used to provide cervical traction to a user's neck.

The terms "comprising," "including," and "having," as used in the claims and specification herein, shall be considered as indicating an open group that may include other elements not specified. The terms "a," "an," and the singular forms of words shall be taken to include the plural form of the same words, such that the terms mean that one or more of something is provided. The term "one" or "single" may be used to indicate that one and only one of something is intended. Similarly, other specific integer values, such as "two," may be used when a specific number of things is intended. The terms "preferably," "preferred," "prefer," "optionally," "may," and similar terms are used to indicate that an item, condition or step being referred to is an optional (not required) feature of the invention.

The invention has been described with reference to various specific and preferred embodiments and techniques. However, it should be understood that many variations and modifications may be made while remaining within the spirit and scope of the invention. It will be apparent to one of ordinary skill in the art that methods, devices, device elements, materials, procedures and techniques other than those specifically described herein can be applied to the practice of the invention as broadly disclosed herein without resort to undue experimentation. All art-known functional equivalents of methods, devices, device elements, materials, procedures and techniques described herein are intended to be encompassed by this invention. Whenever a range is disclosed, all subranges and individual values are intended to be encompassed. This invention is not to be limited by the embodiments disclosed, including any shown in the drawings or exemplified in the specification, which are given by way of example and not of limitation.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

All references throughout this application, for example patent documents including issued or granted patents or equivalents, patent application publications, and non-patent literature documents or other source material, are hereby incorporated by reference herein in their entireties, as though individually incorporated by reference, to the extent each reference is at least partially not inconsistent with the disclosure in the present application (for example, a reference that is partially inconsistent is incorporated by reference except for the partially inconsistent portion of the reference).

We claim:

1. A portable spinal decompression device comprising:
   a. an upper thoracic belt including a thoracic inner wrap belt having a first adjustable closure and an outer tension adjustment and configured to be wrapped around a user's chest, wherein the upper thoracic belt is formed of a stretchable material, and further wherein the first adjustable closure of the thoracic inner wrap belt and the outer tension adjustment are configured to allow a size of the upper thoracic belt to be adjusted when fitting to the user;
   b. a lumbar belt including a lumbar inner wrap belt having a second adjustable closure and configured to be wrapped around the user's waist, wherein the lumbar belt is formed of a stretchable material, and further wherein the second adjustable closure of the lumber inner wrap belt is configured to allow a size of the lumbar belt to be adjusted when fitting to the user;
   c. an upper anchor positioned on the upper thoracic belt and defining a first receiving well;
   d. a lower anchor positioned on the lumbar belt and defining a second receiving well;
   e. a toothed rod having a first end received by the first receiving well of the upper anchor and a second end received by the second receiving well of the lower anchor, wherein each of the first and second ends are enclosed by the respective receiving well, and further wherein the upper and lower anchor are configured to receive and transfer force from the toothed rod; and
   f. a traction assembly capable of extending the toothed rod, wherein the traction assembly is configured to move bi-directionally along the toothed rod and comprises an actuator mechanism including one or more actuator handles and a quick release mechanism, wherein:
      the one or more actuator handles are configured to be selectively moved between a first position, a second position, and a third position, the first position being a raised position, the third position being a fully lowered position, and the second positon being a position between the first and third position;
      the one or more actuator handles are configured to be moved between the first and second position to move the actuator mechanism in a first direction along the toothed rod to facilitate spinal decompression of the spinal column from the upper thoracic region to the lower lumbar region of the spinal column;
      the one or more actuator handles are configured to be moved to the third position to prevent movement of the actuator mechanism in the first direction along the toothed rod; and
      the actuator mechanism is configured to move in a second direction along the toothed rod when the quick release mechanism is actuated.

2. The device of claim 1, wherein the first adjustable closure is configured to adjust a position of the upper anchor relative to the user and the second adjustable closure is configured to adjust a position of the lower anchor relative to the user to ensure a proper fit.

3. The device of claim 1, wherein the toothed rod is extended via a mechanism selected from a group consisting of hydraulic, pneumatic, electric or mechanical.

4. The device of claim 1, wherein the toothed rod is one of at least two toothed rods.

5. A portable spinal decompression device comprising:
   a. an upper thoracic belt configured to be wrapped around a user's entire chest and positioned close to the user's axilla, wherein the upper thoracic belt is at least partially formed of a stretchable material;
   b. a lumbar belt configured to be wrapped around the user's waist, wherein the lumbar belt is at least partially formed of a stretchable material;
   c. one or more rods; and
   d. a traction assembly capable of extending the one or more rods, wherein the traction assembly is configured to move bi-directionally along the one or more rods and comprises an actuator mechanism including one or more actuator handles and a quick release mechanism, wherein:
      the one or more actuator handles are configured to be selectively moved between a first position, a second position, and a third position, the first position being a raised position, the third position being a fully lowered position, and the second positon being a position between the first position and the third position;
      the one or more actuator handles are configured to be moved between the first position and the second position to facilitate movement of the actuator mechanism in a first direction along the one or more rods to facilitate spinal decompression of the spinal column from the upper thoracic region to the lower lumbar region of the spinal column;
      the one or more actuator handles are configured to be moved to the third position to prevent movement of the actuator mechanism in the first direction along the one or more rods; and
      the actuator mechanism is configured to move in a second direction along the one or more rods when the quick release mechanism is actuated.

6. The device of claim 5, further comprising:
   a. An upper anchor positioned on the upper thoracic belt and defining a first receiving well; and
   b. A lower anchor positioned on the lumbar belt and defining a second receiving well, wherein one of the one or more rods includes a first end received by the first receiving well of the upper anchor and a second end received by the second receiving well of the lower anchor, each of the first and second ends being enclosed by the respective receiving well.

7. The device of claim 6, wherein the upper thoracic belt includes a thoracic inner wrap belt having a first adjustable closure and the lumbar belt includes a lumbar inner wrap belt having a second adjustable closure, each of the first and second adjustable closures configured to allow a size of the respective belt to be adjusted when fitting to the user.

8. The device of claim 7, wherein the first adjustable closure is configured to adjust a position of the upper anchor relative to the user and the second adjustable closure is configured to adjust a position of the lower anchor relative to the user to ensure a proper fit.

9. The device of claim 7, wherein the upper thoracic belt further includes a first outer tension adjustment and the lumber belt further includes a second outer tension adjustment.

10. The device of claim 5 wherein the one or more rods are telescoping stock.

11. The device of claim 5 wherein the one or more rods are extended via a mechanism selected from a group consisting of hydraulic, pneumatic, electric or mechanical.

12. The device of claim 5, wherein the one or more rods comprises one or more toothed rods.

13. A method of spinal decompression comprising;
   a. providing a portable device comprising an upper thoracic belt formed of a stretchable material and having a thoracic inner wrap belt and a first outer tension adjustment, a lumbar belt formed of a stretchable material and having a lumbar inner wrap belt and a second outer tension adjustment, one or more rods and a traction tensioner assembly comprising an actuator mechanism with one or more actuator handles and configured to move bi-directionally along the one or more rods when said one or more actuator handles are raised and lowered to facilitate spinal decompression of a user's spinal column from an upper thoracic region to a lower lumbar region of the user's spinal column;
   b. inserting a first end of each of the one or more rods into a respective upper anchor positioned on the upper thoracic belt such that each respective upper anchor receives and transfers force from the first end of the respective rod;
   c. inserting a second end of each of the one or more rods into a respective lower anchor positioned on the lumbar belt such that each respective lower anchor receives and transfers force from the second end of the respective rod;
   d. wrapping the upper thoracic belt around the user's entire chest positioned close to the user's axilla;
   e. wrapping the lumbar belt around the user's waist;
   f. adjusting the upper thoracic belt and the lumbar belt such that the user can stand, sit, or lay down while wearing and operating the portable device, wherein adjusting the upper thoracic belt and the lumbar belt includes adjusting the thoracic inner wrap belt and the lumbar inner wrap belt using a respective closure and cinching the first and second outer tension adjustments;
   g. varying a distance between the upper thoracic belt and the lumbar belt of the portable device by utilizing the actuator mechanism to exert force through the traction tensioner assembly and extend the one or more rods from a neutral position to an activated position to facilitate spinal decompression;
   h. maintaining the one or more rods in the activated position for a time period of use; and
   i. releasing the traction tensioner assembly to move the one or more rods from the actuated position to the neutral position after the time period of use is completed.

14. The method of claim 13 wherein the traction mechanism for extending the one or more rods includes an actuator.

15. The method of claim 14 wherein releasing the traction tensioner assembly to move the one or more rods from the actuated position to the neutral position includes activating a quick release mechanism of the actuation mechanism.

16. The method of claim 13, wherein:
   a. varying a distance between the belts of the portable device by utilizing the actuator mechanism to exert force through the traction tensioner assembly and extend the rods to a position to facilitate spinal decompression further includes moving the one or more actuator handles between a first position and a second position, wherein moving the one or more actuator handles between the first and second positions is configured to move the actuator mechanism in a first direction along the one or more rods; and
   b. maintaining the one or more rods in the position for a time period of use includes moving the one or more actuator handles into a third position, wherein the first position is a raised position, the third position is a fully lowered position, and the second position is a position between the first and third positions.

* * * * *